US008343515B2

(12) United States Patent
Huvard et al.

(10) Patent No.: US 8,343,515 B2
(45) Date of Patent: Jan. 1, 2013

(54) PERFLUOROCARBON GEL FORMULATIONS

(75) Inventors: Gary Huvard, Chesterfield, VA (US); Richard Kiral, Costa Mesa, CA (US); Maxine Quitaro, Chesterfield, VA (US); Deborah P. Thompson, Durham, NC (US); Aharon Grossman, Durham, NC (US); Gary Clauson, Costa Mesa, CA (US); Gurbhagat Sandhu, Manakin-Sabot, VA (US)

(73) Assignee: Oxygen Biotherapeutics, Inc., Costa Mesa, CA (US)

( * ) Notice: Subject to any disclaimer, the term of this patent is extended or adjusted under 35 U.S.C. 154(b) by 453 days.

(21) Appl. No.: 12/590,996

(22) Filed: Nov. 17, 2009

(65) Prior Publication Data

US 2010/0144861 A1   Jun. 10, 2010

Related U.S. Application Data

(63) Continuation-in-part of application No. 12/589,202, filed on Oct. 19, 2009, now abandoned.

(60) Provisional application No. 61/200,254, filed on Nov. 25, 2008, provisional application No. 61/204,785, filed on Jan. 9, 2009, provisional application No. 61/205,499, filed on Jan. 21, 2009.

(51) Int. Cl.
*A61K 9/00* (2006.01)
*A61K 51/00* (2006.01)
*A61M 36/14* (2006.01)

(52) U.S. Cl. ............................. 424/400; 424/1.89
(58) Field of Classification Search .................. 424/400
See application file for complete search history.

(56) References Cited

U.S. PATENT DOCUMENTS

| | | |
|---|---|---|
| 3,911,138 A | 10/1975 | Clark, Jr. |
| 3,977,988 A | 8/1976 | Tokiwa et al. |
| 3,996,141 A | 12/1976 | Updike |
| 4,173,654 A | 11/1979 | Scherer |
| 4,289,499 A | 9/1981 | Clark et al. |
| 4,366,169 A | 12/1982 | White |
| 4,411,872 A | 10/1983 | Bramson |
| 4,452,818 A | 6/1984 | Haidt |
| 4,453,028 A | 6/1984 | Lagow |
| 4,549,969 A | 10/1985 | Gerlach |
| 4,686,024 A | 8/1987 | Scherer, Jr. et al. |
| 4,879,062 A | 11/1989 | Moore |
| RE33,451 E | 11/1990 | Clark, Jr. |
| 5,045,296 A | 9/1991 | Pfeffer et al. |
| 5,158,536 A | 10/1992 | Sekins et al. |
| 5,295,953 A | 3/1994 | Richard et al. |
| 5,300,528 A | 4/1994 | Graybill et al. |
| 5,399,334 A | 3/1995 | Kawakami et al. |
| 5,407,685 A | 4/1995 | Malchesky et al. |
| 5,437,272 A | 8/1995 | Fuhrman |
| 5,490,498 A | 2/1996 | Faithfull |
| 5,578,022 A | 11/1996 | Scherson et al. |
| 5,674,913 A | 10/1997 | Clark, Jr. |
| 5,792,090 A | 8/1998 | Ladin |
| 5,824,703 A | 10/1998 | Clark, Jr. |
| 5,840,767 A | 11/1998 | Clark, Jr. |
| 6,167,887 B1 | 1/2001 | Clark et al. |
| 6,346,228 B1 | 2/2002 | Choudhary et al. |
| 6,767,342 B1 | 7/2004 | Cantwell |
| 6,815,186 B2 | 11/2004 | Clark, Jr. |
| 7,160,553 B2 | 1/2007 | Gibbins et al. |
| 7,767,232 B2 | 8/2010 | Nudler et al. |
| 2003/0069563 A1 | 4/2003 | Johnson |
| 2004/0166171 A1 | 8/2004 | McGrath et al. |
| 2005/0276865 A1 | 12/2005 | Buyuktimkin et al. |
| 2005/0281890 A1 | 12/2005 | San |
| 2007/0026024 A1 | 2/2007 | Drees et al. |
| 2007/0098662 A1 | 5/2007 | Blume et al. |
| 2007/0224169 A1 | 9/2007 | Sliwa, Jr. et al. |
| 2009/0017147 A1 | 1/2009 | Litner et al. |
| 2009/0169630 A1 | 7/2009 | Ward et al. |
| 2009/0202617 A1 | 8/2009 | Ward et al. |
| 2011/0086923 A1 | 4/2011 | Thompson et al. |
| 2011/0229575 A1 | 9/2011 | Clauson et al. |
| 2011/0230566 A1 | 9/2011 | Tamergo et al. |

FOREIGN PATENT DOCUMENTS

| | | |
|---|---|---|
| EP | 0091820 | 10/1983 |
| EP | 0521492 | 1/1993 |
| WO | WO/92/19232 | 11/1992 |
| WO | WO/95/31191 | 11/1995 |
| WO | WO/97/19678 | 6/1997 |
| WO | WO/97/38579 | 10/1997 |
| WO | WO/99/26604 | 6/1999 |
| WO | WO/2004/028677 | 4/2004 |
| WO | WO/2007/134304 | 11/2007 |
| WO | WO/2009/102487 | 8/2009 |
| WO | WO/2010/008594 | 1/2010 |
| WO | WO/2010/033187 | 3/2010 |
| WO | WO/2010/099107 | 9/2010 |

OTHER PUBLICATIONS

U.S. Appl. No. 13/250,682, filed Sep. 30, 2011, Gerald Klein.
PCT International Preliminary Report on Patentability issued Aug. 17, 2010 in connection with PCT international Application No. PCT/US2009/00946.
PCT International Search Report issued Sep. 16, 2010 in connection with PCT International Application No. PCT/US2010/02106.
PCT International Preliminary Report on Patentability issued Jan. 18, 2011 in connection with PCT International Application No. PCT/US2009/04165.
PCT International Preliminary Report on Patentability issued Mar. 22, 2011 in connection with PCT International Application No. PCT/US2009/05162.
PCT International Search Report issued May 5, 2011 in connection with PCT International Application No. PCT/US2011/28980.

(Continued)

*Primary Examiner* — Sreeni Padmanabhan
*Assistant Examiner* — Layla Soroush
(74) *Attorney, Agent, or Firm* — Gary J. Gershik; Cooper & Dunham LLP

(57) ABSTRACT

A perfluorocarbon gel composition is disclosed with numerous uses including topical medical and cosmetic uses.

23 Claims, 6 Drawing Sheets

OTHER PUBLICATIONS

Written Opinion of the International Searching Authority issued May 5, 2011 in connection with PCT International Application No. PCT/US2011/28980.

PCT International Preliminary Report on Patentability issued May 31, 2011 in connection with PCT International Application No. PCT/US2009/006159.

Office Action issued Feb. 23, 2011 in connection with U.S. Appl. No. 12/378,460.

Office Action issued May 23, 2011 in connection with U.S. Appl. No. 12/378,460.

Mar. 23, 2011 Communication in Response to Feb. 23, 2011 Office Action issued in connection with U.S. Appl. No. 12/378,460.

Chinese Office Action issued Oct. 9, 2010 in connection with Chinese Patent Application No. 200780017595.X (including English Translation).

Jan. 29, 2010 Response to Sep. 1, 2009 Japanese Office Action issued in connection with Japanese Patent Application No. 2000-521806 (including English language draft).

Tütüncü, A.S. et al. (1993) "Comparison of Ventilatory Support with Intratracheal Perfluorocarbon Administration . . ." American Review of Respiratory Disease. (148):785-792.

Weinkle (2010) Efficacy and Tolerability of Admixing 0.3% Lidocaine with Dermicol-P35 270 for the Treatment of Nasolabial Folds, Dermatologic Surgery. 36(3):316-320.

U.S. Appl. No. 12/460,409, filed Jul. 17, 2009, Bullock et al.

U.S. Appl. No. 12/589,202, filed Oct. 19, 2009, Huvard et al.

U.S. Appl. No. 12/653,343, filed Dec. 10, 2009, Ward et al.

U.S. Appl. No. 12/761,379, filed Apr. 15, 2010, Kiral et al.

PCT International Search Report issued on Aug. 27, 1999 in connection with International Application No. PCT/US1998/24632.

PCT International Search Report issued on Oct. 17, 2007 in connection with International Application No. PCT/US2007/068910.

PCT International Search Report issued on Apr. 21, 2009 in connection with International Application No. PCT/US2009/00946.

PCT International Search Report issued on Nov. 6, 2009 in connection with International Application No. PCT/US2009/05162.

PCT International Search Report issued on Dec. 9, 2009, in connection with International Application No. PCT/US2009/05715.

PCT International Search Report issued on Feb. 12, 2010 in connection with International Application No. PCT/US2009/06159.

PCT International Preliminary Report on Patentability issued on Nov. 17, 2008 in connection with PCT International Application No. PCT/US2007/068910.

Written Opinion of the International Searching Authority issued on Oct. 17, 2007 in connection with International Application No. PCT/US2007/068910.

Written Opinion of the International Searching Authority issued on Apr. 21, 2009 in connection with International Application No. PCT/US2009/00946.

Written Opinion of the International Searching Authority issued on Nov. 6, 2009 in connection with International Application No. PCT/US2009/05162.

Written Opinion of the International Searching Authority issued on Dec. 9, 2009 in connection with International Application No. PCT/US2009/05715.

Written Opinion of the International Searching Authority issued on Feb. 12, 2010 in connection with International Application No. PCT/US2009/06159.

Japanese Office Action issued Sep. 1, 2009 in connection with Japanese Patent Application No. 2000-521806 (including English translation).

Bekyarova G (1997) "Suppressive effects of FC-43 perfluorocarbon emulsion on enhanced oxidative haemolysis in the early postburn phase" Burns. 23(2):117-121.

Clark L. et al. (1979) "A New Look at the Vapor Pressure Problem in . . ." Int. Congr. Ser.—Excerpta: 486 (Proc. Int. Symp. Perfluorochem. Blood Substitutes, 4th): 55-67.

Clark, Jr. et al. (1989) "Physiological Evaluation of Fluorocarbon Emulsions with Notes on F-Decalin and Pulmonary Inflation . . ." Mat. Res. Soc. Symp. Proc.: 129-134.

Lin, Wen-Huey and Richard J. Laow (1990) "The Synthesis of Highly Fluorinated Alkycyclohexanes for Use as Oxygen Casrriers and the . . ." Journal of Fluorine Chemistry. 50:345-35.

Moore, R. E. et al. (1982) "Synthesis and Physical Properties of Perfluorocompounds Useful as Synthetic Blood . . ." Oxygen Carrying Colloidal Blood Substitutes: 50-60.

Okamoto H. et al. (1984) "Fate of perfluorochemical impurities contained in both perfluorodecaline (FDC) and perfluorotripropylamine (FTPA) in . . ." Chemical Abstracts. (100):3.

Smith et al. (1997) "Partial Liquid Ventilation: a Comparison Using Conventional and High Frequency Techniques in an Animal Model of . . ." Crit Care Med. 25(7):1179-1186.

Varushchenko, RM, et al. (1996) "Thermodynamics of Vaorization of Some Cyclic Perfluorocarbons" Fluid Phase Equilibria, 126(1996) 93-104.

Jul. 25, 2012 Chinese Office Action issued in connection with Chinese Patent Application No. 200980147692.X (including English language translation).

Aug. 23, 2012 Office Action issued in connection with U.S. Appl. No. 12/761,379.

PERFLUOROCARBON GEL FORMULATIONS

This is a continuation-in-part of U.S. patent application Ser. No. 12/589,202, filed Oct. 19, 2009, now abandoned and claims the benefit of 1) U.S. Provisional Application No. 61/205,499, filed Jan. 21, 2009, 2) U.S. Provisional Application No. 61/204,785, filed Jan. 9, 2009, and 3) U.S. Provisional Application No. 61/200,254, filed Nov. 25, 2008, the entire content of each of which is hereby incorporated by reference herein.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Perfluorocarbons (PFCs) possess the ability to dissolve large quantities of many gases at concentrations much larger than water, saline and plasma. In addition, PFCs can transport these gases to diffuse across distances. Thus, PFCs can be a convenient and inexpensive means to deliver high levels of oxygen or other therapeutic gases to tissues and organ systems.

PFCs that are commonly used in medical research are non-toxic, biologically inert, biostatic liquids at room temperature with densities of about 1.5-2.0 g/mL and high solubilities for oxygen and carbon dioxide. Such PFCs have been found to be efficient carriers of gases, both as emulsions for intravenous use and as neat liquids for liquid ventilation applications.

SUMMARY OF THE INVENTION

The subject application provides for a perfluorocarbon gel composition comprising 10-90 wt % perfluorocarbon and 8-70 wt % water relative to the total weight of the gel.

The subject application also provides, for a method of continuously delivering oxygen to a tissue at a rate of 0.2 cc/hour-20.0 cc/hour for up to 24 hours by contacting the tissue with a perfluorocarbon gel composition described herein.

The subject application also provides for a method of treating a wound, a burn injury, acne or rosacea in a subject suffering therefrom comprising topically administering to the skin of the subject a perfluorocarbon gel composition described herein effective to treat the subject's wound, burn injury, acne or rosacea.

The subject application also provides for a method of increasing the firmness of the skin or reducing the appearance of fine lines, wrinkles or scars in a subject comprising topically administering to the skin of the subject a perfluorocarbon gel composition described herein effective to increase the firmness of the subject's skin or reduce the appearance of fine lines, wrinkles or scars on the subject's skin.

The subject application also provides for a method of manufacturing a perfluorocarbon gel composition comprising the steps: a) mixing aqueous phase components in a vessel; b) homogenizing the mixture; c) adding perfluorocarbon to the mixture over time during high speed homogenization; and d) obtaining the gel.

BRIEF DESCRIPTION OF THE DRAWINGS

FIG. 5 shows the concentration of oxygen in the water in FIG. 4 as time goes on.

DETAILED DESCRIPTION OF THE INVENTION

Embodiments of the Invention

Figure 1:
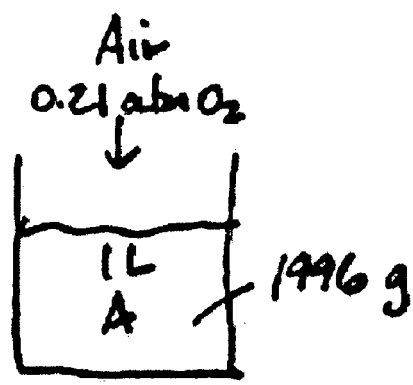
FIG. 1 shows the schematic of an experiment as described herein where a liter of liquid A (perfluoro(tert-butylcyclohexane) or "FtBu") and a liter of liquid B (water), each initially void of oxygen, are allowed to absorb oxygen from the air.
Figure 1:
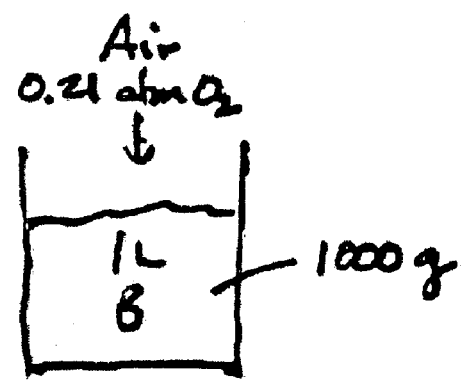

The subject application provides for a perfluorocarbon gel composition comprising 10-90 wt % perfluorocarbon and 8-70 wt % water relative to the total weight of the gel.

In one embodiment, the perfluorocarbon is perfluoro(tert-butylcyclohexane). In another embodiment, the perfluorocarbon is perfluorodecalin. In another embodiment, the perfluorocarbon is trimethyl perfluorodecalin or perfluoroisopropyldecalin.

In yet another embodiment, the composition further comprises 1-5 wt % surfactants. In another embodiment, the surfactants include polyoxyethylene-polyoxypropylene block copolymers. In another embodiment, the polyoxyethylene-polyoxypropylene block copolymers include Poloxamer 105 and/or Poloxamer 188.

In one embodiment, the composition further comprises 0.01-10 wt % Vitamin E. In another embodiment, the composition comprises 0.03 wt % Vitamin E.

In one embodiment, the composition further comprises 0.02-3.20 wt % preservatives. In another embodiment, the preservatives include poly(diallyldimethylammonium chloride), poly(acrylamide-co-diallyldimethylammonium chloride) and/or ethylene diamine ttetraacetic acid.

In one embodiment, the composition comprises 90 wt % perfluorocarbon, 8 wt % water, and 2 wt % surfactants. In another embodiment, the composition comprises 30-50 wt % perfluorocarbon, 48-70 wt % water, and 2 wt % surfactants. In another embodiment, the composition comprises 86.86 wt % perfluorocarbon, 10.42 wt % water, 2.69 wt % surfactants and 0.03 wt % Vitamin E. In yet another embodiment, the composition comprises 86.86 wt % perfluoro(tert-butylcyclohexane), 10.42 wt % water, 2.43 wt % Poloxamer 105, 0.26 wt % Poloxamer 188 and 0.03 wt % Vitamin E.

In one embodiment, the preservatives include 0-0.40 wt % poly(diallyldimethylammonium chloride), 0.01-0.80 wt % poly(acrylamide-co-diallyldimethylammonium chloride) and 0.01-2.00 wt % ethylene diamine tetraacetic acid. In another embodiment, the composition comprises 84-88 wt % perfluoro(tert-butylcyclohexane), 9-11 wt % water, 2-3 wt % Poloxamer 105, 0.01-1 wt % Poloxamer 188, 0-0.40 wt % poly(diallyldimethylammonium chloride), 0.01-0.80 wt % poly(acrylamide-co-diallyldimethylammonium chloride) and 0.01-2.00 wt % ethylene diamine tetraacetic acid.

In one embodiment, the composition comprises 85.98 wt % perfluoro(tert-butylcyclohexane), 10.28 wt % water, 2.45 wt % Poloxamer 105, 0.31 wt % Poloxamer 188, 0.74 wt % poly(acrylamide-co-diallyldimethylammonium chloride) and 0.25 wt % ethylene diamine tetraacetic acid.

In one embodiment, the composition comprises 86.73 wt % perfluoro(tert-butylcyclohexane), 10.37 wt % water, 2.47 wt % Poloxamer 105, 0.31 wt % Poloxamer 188, 0.10 wt % poly(acrylamide-co-diallyldimethylammonium chloride) and 0.03 wt % ethylene diamine tetraacetic acid.

In one embodiment, the composition comprises 85.98 wt % perfluoro(tert-butylcyclohexane), 10.28 wt % water, 2.45 wt % Poloxamer 105, 0.31 wt % Poloxamer 188, 0.25 wt % poly(diallyldimethylammonium chloride), 0.50 wt % poly(acrylamide-co-diallyldimethylammonium chloride) and 0.25 wt % ethylene diamine tetraacetic acid.

In one embodiment, the composition comprises 86.73 wt % perfluoro(tert-butylcyclohexane), 10.37 wt % water, 2.47 wt % Poloxamer 105, 0.31 wt % Poloxamer 188, 0.03 wt % poly(diallyldimethylammonium chloride), 0.07 wt % poly(acrylamide-co-diallyldimethylammonium chloride) and 0.03 wt % ethylene diamine tetraacetic acid.

In one embodiment, the composition further comprises 0.10-2 wt % copper. In another embodiment, the copper is copper (II) oxide.

In one embodiment, the perfluorocarbon gel composition is characterized by that it continuously delivers oxygen to a tissue at a rate of 0.2 cc/hour-20.0 cc/hour for up to 24 hours. In another embodiment, the perfluorocarbon composition continuously delivers oxygen to the tissue at a rate of 2.0 cc/hour for 24 hours. In yet another embodiment, the perfluorocarbon gel composition further comprises urea hydrogen peroxide.

The subject application also provides for a method of continuously delivering oxygen to a tissue at a rate of 0.2 cc/hour-20.0 cc/hour for up to 24 hours by contacting the tissue with a perfluorocarbon gel composition described herein.

The subject application also provides for a method of treating a wound, a burn injury, acne or rosacea in a subject suffering therefrom comprising topically administering to the skin of the subject a perfluorocarbon gel composition described herein effective to treat the subject's wound, burn injury, acne or rosacea.

The subject application also provides for a method of increasing the firmness of the skin or reducing the appearance of fine lines, wrinkles or scars in a subject comprising topically administering to the skin of the subject a perfluorocarbon gel composition described herein effective to increase the firmness of the subject's skin or reduce the appearance of fine lines, wrinkles or scars on the subject's skin.

The subject application also provides for a process of manufacturing a perfluorocarbon gel composition comprising the steps: a) mixing aqueous phase components in a vessel; b) homogenizing the mixture; c) adding perfluorocarbon to the mixture over time during high speed homogenization; and d) obtaining the gel.

In one embodiment, in step a) the aqueous phase components include distilled water, surfactants and/or preservatives. In another embodiment, in step a) the vessel is a glass, polyethylene, PET, or stainless steel vessel.

In one embodiment, in step b) the homogenizer is a rotor stator homogenizer. In another embodiment, in step b) the mixture is homogenized for 4-6 minutes. In another embodiment, in step b) the mixture is homogenized for 5 minutes. In yet another embodiment, in step b) the mixture is homogenized at 10,000-35,000 RPM.

In on embodiment, in step c) the perfluorocarbon is added in aliquots or continuously over 10-30 minutes.

In one embodiment, the perfluorocarbon is perfluoro(tert-butylcyclohexane).

All combinations of the various elements described herein are within the scope of the invention.

The biochemistry of wound healing and strategies for wound treatment is described Chin et al., (2007) "Biochemistry of Wound Healing in Wound Care Practice" *Wound Care Practice*, 2$^{nd}$ ed., Best Publishing, AZ., which is hereby incorporated by reference.

Acne treatments are described in section 10, chapter 116, pp 811-813 of The Merck Manual, 17$^{th}$ Edition (1999), Merck Research Laboratories, Whitehouse Station, N.J., U.S.A. which is hereby incorporated by reference.

Terms

As used herein, and unless stated otherwise, each of the following terms shall have the definition set forth below.

"Accelerates healing" as used herein means an increased rate of burn injury/wound repair and healing as compared to the rate of burn injury/wound repair and healing in an untreated control subject.

"Administering to the subject" means the giving of, dispensing of, or application of medicines, drugs, or remedies to a subject to relieve or cure a pathological condition. Topical administration is one way of administering the instant compounds and compositions to the subject.

"Ameliorating" a condition or state as used herein shall mean to lessen the symptoms of that condition or state. "Ameliorate" with regard to skin comedones, pustules or papules is to reduce the discomfort caused by comedones, pustules or papules and/or to reduce their appearance and/or physical dimensions.

"Antibacterial agent" means a bactericidal compound such as silver nitrate solution, mafenide acetate, or silver sulfadiazine, or an antibiotic. According to the present invention, antibacterial agents can be present in "Curpon™" products. "Cupron™" products utilize the qualities of copper and binds copper to textile fibers, allowing for the production of woven, knitted and non-woven fabrics containing copper-impregnated fibers with the antimicrobial protection against microorganisms such as bacteria and fungi.

"Biologically active agent" means a substance which has a beneficial or adverse effect on living matters.

"Burn wound" means a wound resulting from a burn injury, which is a first, second or third degree injury caused by thermal heat, radiation, electric or chemical heat, for example as described at page 2434, section 20, chapter 276, of The Merck Manual, 17$^{th}$ Edition (1999), Merck Research Laboratories, Whitehouse Station, N.J., U.S.A.

"Effective" as in an amount effective to achieve an end means the quantity of a component that is sufficient to yield a desired therapeutic response without undue adverse side effects (such as toxicity, irritation, or allergic response) commensurate with a reasonable benefit/risk ratio when used in the manner of this disclosure. For example, an amount effective to promote wound healing without causing undue adverse side effects. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

"Gel" means a semi-solid or solid colloid (depending on concentration and/or temperature) of a solid/semi-solid and a liquid wherein a liquid dispersed phase is dispersed in a solid/semi-solid continuous medium. Some gels become fluids due to agitation then resume their gel structure when allowed to be undisturbed. Common pharmaceutical gels are solids which when applied and with motion allow the product to become temporarily a liquid phase so it applies smoothly, then becomes tacky then dries. Other gels are semi solid which are a semi-liquid, semi-solid mixture & when applied become tacky then dry. "Hydrogel" means any colloid in which the particles are in the external dispersion phase and water is in the internal dispersed phase.

"Infection" as used in respect to *Propionibacterium acnes* means a detrimental colonization of the (host) subject by the *Propionibacterium acnes* causing an inflammation response in the subject.

"Oxygen tension" or "tissue oxygen tension" is the directly measured local partial pressure of oxygen in a specific tissue.

"Oxygenated perfluorocarbon" is a perfluorocarbon which is carrying oxygen at, for example, saturation or sub-saturation levels.

"Pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject. The carrier may be liquid or solid and is selected with the planned manner of administration in mind.

"Pharmaceutically active compound" means the compound or compounds that are the active ingredients in a pharmaceutical formulation.

"Promotes alleviation of pain" means a decrease in the subject's experience of pain resulting from a wound or an injury, e.g., a burn injury.

"Sex organ" or "sexual organ" means any of the anatomical parts of the body which are involved in sexual reproduction and constitute the reproductive system in a complex organism. In a preferred embodiment of this invention, the sex organ is the genitalia of the subject. As used herein, the "genitalia" refer to the externally visible sex organs: in males the penis, in females the clitoris and vulva.

"Surfactants" means wetting agents that lower the surface tension of a liquid, allowing easier spreading, and lower the interfacial tension between two liquids. According to one embodiment of the present invention, the surfactants can be Poloxamer 105 (available from BASF Corporation of Mt. Olive, N.J. as Pluronic® L35) or Poloxamer 188 (available from BASF Corporation of Mt. Olive, N.J. as Pluronic® F68) Poloxamer 188 or Poloxamer 407, or a mixture thereof.

"Topical administration" of a composition as used herein shall mean application of the composition to the skin of a subject. In an embodiment, topical administration of a composition is application of the composition to the epidermis of a subject.

"wt %" when referring to the percentage of a component in the gel is percentage of the weight of the component in the gel relative to the total weight of the gel.

Perfluoro(tert-butylcyclohexane)

PFCs include perfluoro(tert-butylcyclohexane) ($C_{10}F_{20}$, CAS No. 84808-64-0) which is available, for example, as Oxycyte™ from Oxygen Biotherapeutics Inc., Costa Mesa, Calif. In an embodiment, the perfluoro(tert-butylcyclohexane) has the following structure:

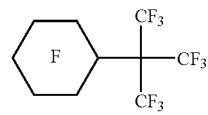

Physical properties of perfluoro(tert-butylcyclohexane) are as follows:

| | |
|---|---|
| Molecular Formula | $C_{10}F_{20}$ |
| Molecular Weight (g/mol) | 500.08 |
| Physical State @ Room Temp. | Liquid |
| Density (g/mL) | 1.97 |
| Boiling Point (° C.) | 147 |
| Vapor Pressure (mmHg) @ 25° C. | 3.8 |
| Vapor Pressure (mmHg) @ 37° C. | 4.4 |
| Kinematic Viscosity (cP) | 5.378 |
| Refractive Index @ 20° C. | 1.3098 |
| Calculated Dipole Moment (Debye) | 0.287 |
| Calculated Surface Tension (dyne/cm) | 14.4 |

Perfluoro(tert-butylcyclohexane) carries about 43 mL of oxygen per 100 mL of PFC, and 196 mL of $CO_2$ per 100 mL of PFC.

Oxycyte™ is a perfluorocarbon emulsion oxygen carrier. The active ingredient in Oxycyte™, perfluoro(tert-butylcyclohexane) ($C_{10}F_{20}$, MW~500), also known as F-tert-butylcyclohexane or "FtBu", is a saturated alicyclic PFC. Perfluoro(tert-butylcyclohexane) is a colorless, completely inert, non-water soluble, non-lipophilic molecule, which is twice as dense as water, and boils at 147° C. Oxycyte can be used in the PFC compositions, methods and uses described herein.

Being that the PFCs are slightly lipophilic at body temperature and would help in the transport of oxygen into and removal of carbon dioxide from the skin tissue, PFCs can accelerate the healing process of a wound in a tissue. Perfluoro(tert-butylcyclohexane) is only slightly lipophilic at body temperature and not lipophilic at room temperature.

The perfluoro(tert-butylcyclohexane) Gel

In one embodiment of the present invention, the gel is formulated as follows:

| Component | grams | Wt % |
|---|---|---|
| Vitamin E | 0.017 g | 0.03 (300 ppm) |
| Pluronic ® L35 | 1.4 g | 2.43 |
| Pluronic ® F68 | 0.15 g | 0.26 |
| Water | 6.0 g | 10.42 |
| perfluoro(tert-butylcyclohexane) | 50 g | 86.86 |

The perfluorocarbon gel compositions and methods of manufacturing the same disclosed herein are advantageous over existing gels and methods. Initial attempts to make the PFC gel have not been successful. Further, existing methods for making perfluorocarbon gels provide for yields of 15-20% at best. The method disclosed herein provides yields of 80-100%. Through research and experiments the inventors of the subject have successfully manufactured the instant gel with high yields.

The PFC gel composition disclosed herein can be used as a vehicle to deliver oxygen to various tissues, e.g., skin. The PFC composition disclosed herein can concentrate atmospheric oxygen as well as be pre-loaded with molecular oxygen. The composition can deliver oxygen to a tissue or a wound via a diffusion gradient.

It is known that cells need oxygen to regenerate and thrive. Therefore, the PFC gel described herein has numerous applications and can be used where oxygen delivery to the cells in a tissue e.g., aging or damaged skin tissue, is desired.

An Anecdotal Observation and Brief Discussion of PFC Mechanism of Action

A mixture of APF-200 gel (Multifluor® APF-200 perfluoroisopropyldecalin, which is commercially available from Air Products and Chemicals, Inc., Allentown, Pa.) with PLURONIC® L35 liquid was applied to a scratch on a subject which was very red and sore.

Within about three hours of the application, the subject reported that much of the soreness had disappeared and the redness had abated. The subject then applied more gel to the scratch.

The next morning, the long tail of the scratch was almost invisible and the main cut had a small scab and almost no redness. More gel was applied to the scratch that night and by the next morning, the scratch had completely healed with no signs of scarring.

What the PFC Gel is and is Not Doing

Figure 2:
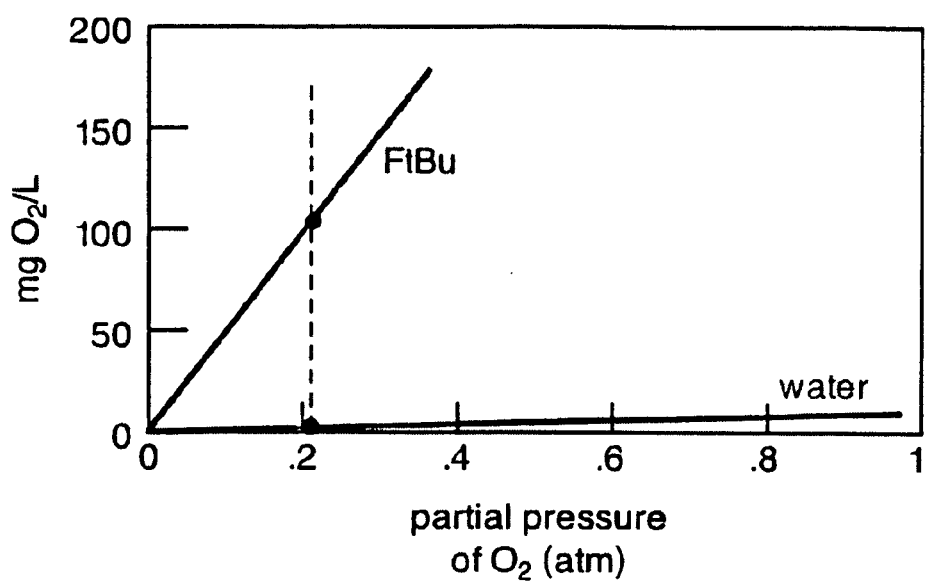
FIG. 2 shows Henry's Law sorption isotherms for perfluoro(tert-butylcyclohexane) and water. The amount of dissolved oxygen in the liquid is measured after equilibration with a gas. The partial pressure of the gas (here, oxygen) is varied. The partial pressure of oxygen in air is 0.21 atm.

Consider the experiment sketched in FIG. 1: Two liquids, FtBu and water, are allowed to absorb oxygen from air. The amount of oxygen dissolved in each when the liquids are at equilibrium with the oxygen in the air can be found from the Henry's Law sorption isotherms for the liquids sketched in FIG. 2.

When the solubility of a gas in a liquid is measured, the solubility is nearly always a linear function of the partial pressure of the gas.

For FtBu, the Henry's law constant is about 600 mg $O_2$/L/atm; that for water is about 8.3 mg $O_2$/L/atm. In contact with air ($O_2$ at 0.21 atm), FtBu holds about 126 mg $O_2$ and water about 1.7 mg/L, both at 25° C. Now convert these values to a weight basis using the density of FtBu (1966 g/L) and water (1000 g/L):

$$\frac{126 \text{ mg}}{L} \Big| \frac{1 \text{ L}}{1966 \text{ g}} = 0.0631 \text{ mg } O_2/\text{g for } FtBu$$

$$\frac{1.7 \text{ mg}}{L} \Big| \frac{1 \text{ L}}{1000 \text{ g}} = 0.0017 \text{ mg } O_2/\text{g for water}$$

Assume the two liquids are mixed together (assuming that FtBu and water are miscible) and determine how much oxygen is in the mixture. First, determine weight fractions of each liquid in the mix:

$$\frac{1966 \text{ g } FtBu}{1966 \text{ g } FtBu + 1000 \text{ g water}} = 0.6628 \text{ g } FtBu/\text{g mix};$$

therefore 0.3372 g water/g mix

When the liquids are mixed, assume that they are unaware of each other, that is, assume that there are no specific molecular interactions that occur. It is known that water can have very strong interactions with many other solvents due to hydrogen-bonding (for example). However, since it is to be assumed that the two liquids are miscible in order to make a simple point, it is easier to assume that they do not interact as well. This is likely a valid assumption given the inertness of the PFC. Under these conditions, the rule of volume additivity holds and the solubility in the mixture as a weighted average of the solubilities in the pure liquids can be computed:

$$0.6628 \frac{\text{g } FtBu}{\text{g mix}} \Big| 0.0631 \frac{\text{mg } O_2}{\text{g } FtBu} + 0.3372 \frac{\text{g water}}{\text{g mix}} \Big| 0.0017 \frac{\text{mg } O_2}{\text{g water}} = 0.0424 \frac{\text{mg } O_2}{\text{g mix}}$$

Mixing an oxygen-binding PFC with water (if that were physically possible) will always give a mixture having a higher oxygen concentration than water alone. The weighted average calculation appears to hold for other gels that were made by the inventors. The oxygen concentrations measured by the inventors for gels made are in the range of 90-95% of what is expected based on the gel composition and the known solubilities of oxygen in FtBu and in water. The difference may lie in the difficulty of fully saturating a gel with oxygen from the air without simultaneously evaporating some of the water and impacting the composition of the gel.

Figure 3:
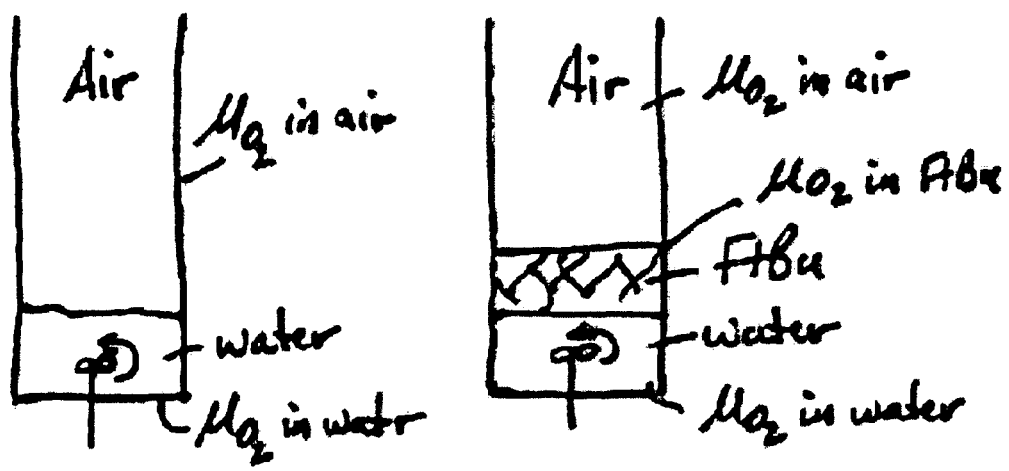
FIG. 3 shows a schematic of a thought experiment. The perfluoro(tert-butylcyclohexane) is actually heavier than water and would sink if it is tried. The purpose of this thought experiment is to determine if the concentration of oxygen in the water is different at equilibrium if a layer of perfluoro(tert-butylcyclohexane) is placed on top of the water.

Now, assume the water in the previous example is replaced with wound tissue (which is mostly water) and consider FIG. 3. The inventors are interested in determining the concentrations of oxygen in the water at equilibrium when FtBu is and is not present between water and the air.

Thermodynamics teaches that equilibrium exists between separate phases in intimate contact when the chemical potential (denoted by μ) is exactly the same in each phase. At a given temperature, the chemical potential of oxygen in air will depend only on the composition—which is fixed. Thus, the chemical potential of oxygen in air for the two scenarios in FIG. 3 must be equivalent if the very small contribution of FtBu vapor in the second case is neglected. If $\mu O_2$ is the same as in air in both cases and if the air and water are in equilibrium in both cases, then $\mu O_2$ in the water must also be the same in each case (again, neglecting the tiny solubility of FtBu in the water in the second case). As for the air, $\mu O_2$ in the water depends only on the temperature and concentration of $O_2$, therefore the concentration of oxygen in the water must be identical in both cases. It makes no difference how much oxygen is dissolved in the FtBu nor does it matter how much FtBu there is. In each case, the amount of oxygen in the water must be identically the same (or very nearly so as the FtBu residuals in the air and water will have a calculable but probably immeasurable impact). It can be concluded that putting on a layer of PFC gel ON TOP OF wound tissue cannot increase the concentration of oxygen IN the wound tissue.

Figure 4:
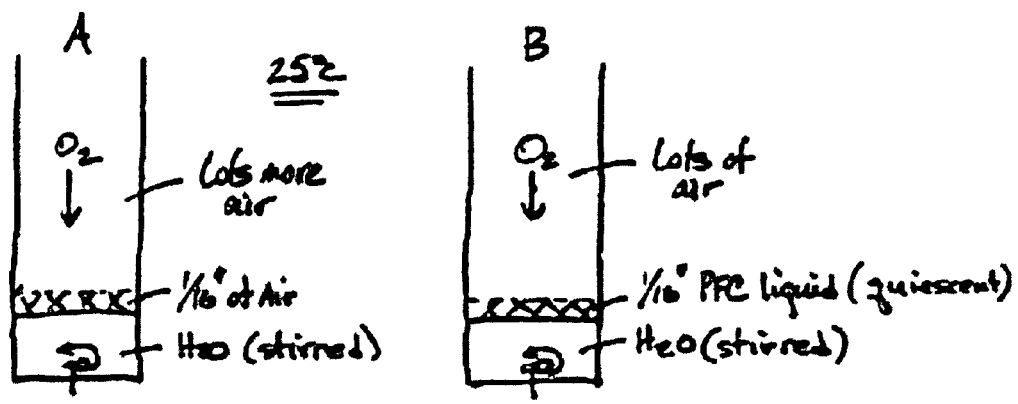
FIG. 4 shows another thought experiment. In case A, there is a small amount of well-stirred water in contact with air. However, the air is divided into two layers.

Now consider FIG. 4. The air in the 1/16" layer in case A is identical to the air above but we will assume that we can diffuse oxygen through this layer independently. In B, replace the thin layer of gas with an equally thin layer of perfluorocarbon liquid. Now, suppose the experiment begins with the water in each case completely devoid of oxygen but saturated with nitrogen so that no nitrogen diffusion occurs in any direction. For the PFC, consider the case when the PFC is initially devoid of $O_2$ and compare that to the case when the PFC is saturated with $O_2$ (but still none in the water). Once the oxygen start diffusing through the air layer and through the PFC and begin dissolving in the water, if the concentration in the water in each case is measured and the values are plotted versus time, the graph may look like FIG. 5 (qualitatively).

Figure 5:
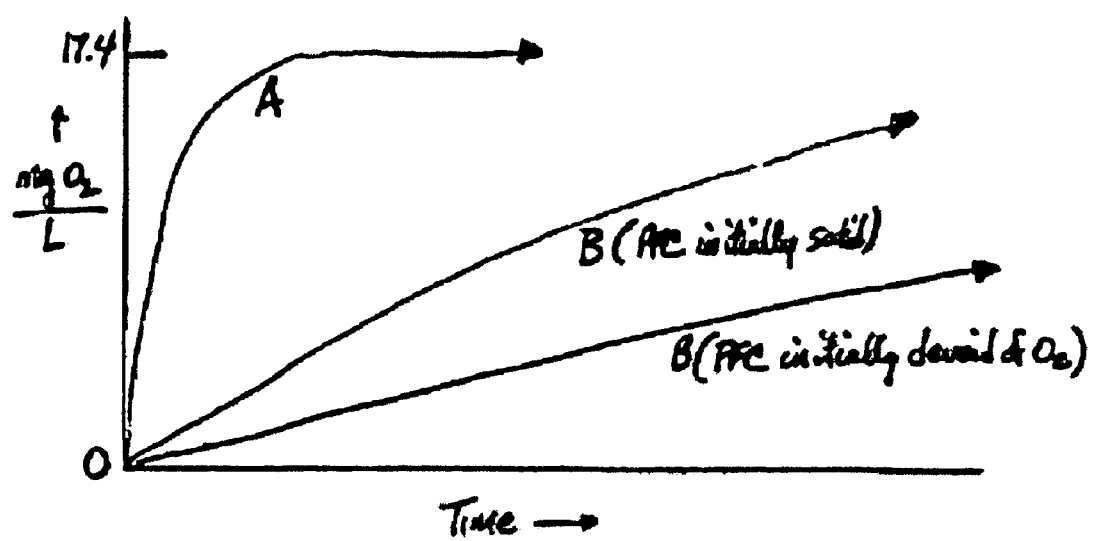
Figure 6:
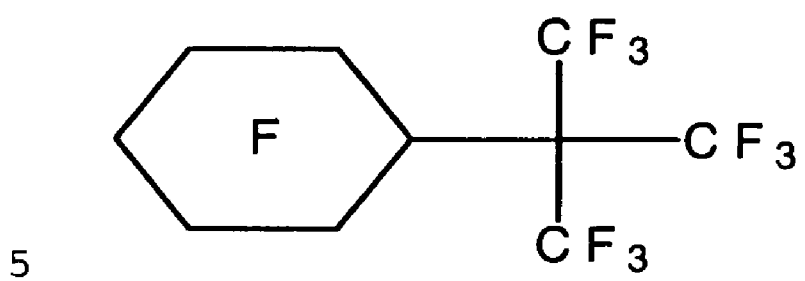
FIG. 6 is a representation of the chemical structure of perfluoro(tert-butylcyclohexane)

To draw FIG. 5, it is only necessary to know that the diffusion coefficient of a gas through a gas is on the order of $10^{-1}$ $cm^2$/s while that for a gas diffusing through a liquid is on the order of $10^{-5}$ $cm^2$/s. For a gas diffusing through a high viscosity gel, the diffusion coefficient might drop to as low as $10^{-6}$ cm$^2$/s or lower depending on how viscous the gel is. That is, the movement of oxygen through the FtBu layer will be at least 10,000 times slower than the movement of oxygen through the equivalently thick air layer in case A. It must necessarily take a good deal longer to saturate the water in case B than in case A, all else being the same. For the two B curves, it is recognized that there is 1) a finite time required to get the oxygen to break through to the other side of the FtBu in the initially O$_2$ devoid layer and 2) the very high capacity of FtBu for oxygen makes the initially devoid layer a "sink" that removes some of the diffusing oxygen from the "stream" making its way to the water. Therefore, it must take longer to saturate the water if the FtBu is also initially devoid of oxygen.

Therefore, the substantial difference in the diffusion coefficients for gases diffusing through gases as opposed to gases diffusing through liquids eliminates the possibility that a layer of FtBu placed on top of a wound "speeds up" the delivery of oxygen to the tissue. In fact, such a layer will substantially slow the delivery rate. This in no way implies that the tissue would be "starved" for oxygen. It is entirely likely that oxygen can diffuse through a thin layer of FtBu at a rate that greatly exceeds the rate of consumption of oxygen by the tissue. Thus, FtBu layer on top of the tissue cannot speed up the delivery process but it doesn't necessary deprive the tissue of oxygen.

So, if the PFC layer on top of the tissue cannot change the concentration of oxygen in the tissue and cannot speed the delivery of oxygen to the tissue, how can we rationalize the anecdotal evidence that PFCs actually do speed up healing. The answer may lie in the fact that PFCs do not stay ON TOP of the skin. When a bit of PFC or one of the gels is rubbed onto the skin, the liquids seem to absorb into the skin within minutes. The gels made with F68 (solid poloxamer) leave a tacky film of F68 (the F68 "bloom") on the surface within 2-3 minutes after application. The gels made with L35 liquid poloxamer are more pleasant and seems to absorb slower than does the PFC and water but eventually disappears as well.

Now return to the first experiment and calculation, but this time, replace the water with tissue. Suppose the PFC absorbs quickly into the tissue and either carries bound $O_2$ with it or independently absorbs diffusing oxygen, in either case, the PFC will increase the average oxygen concentration in the tissue/PFC mixture that forms.

Now the question becomes, from the tissue's perspective, is there any difference in a higher average $O_2$ concentration obtained by mixing a PFC as opposed to raising the external $O_2$ partial pressure in a hyperbaric chamber pressure? This question is tested in Example 3.

Wound and Burns Healing and Scar Prevention and Reduction

As discussed, the PFC gel described herein has numerous applications. For example, the PFC gel disclosed herein can be used as a protective wound covering or a topical gel wound dressing. The wound covering or gel wound dressing can be used with or incorporated into a bandage. The topical gel wound dressing can be used for an approximately 24 hour period to increase availability of Oxygen to the skin surface in wounds such as abrasions, minor lacerations, minor cuts, or minor scalds and burns. The gel can be applied to humans or for veterinary use.

Oxygen is key for healing wounds. Wounds do not heal when oxygen is blocked or decreased (e.g., due to broken capillaries). The topically applied PFC gel creates an oxygen rich environment, increasing oxygen concentration in the affected skin tissue, allowing cells to multiply and heal.

The PFC gel can also be used in treating burn injuries. Extra oxygen in blood promotes angiogenesis, the formation of new capillaries. For severely burned subjects, the PFC gel can not only provide oxygen to oxygen-starved unburned tissue but also promote the establishment of new capillary beds that feed newly grafted skin and burned but salvageable skin. Further, studies have shown that PFCs suppress early postburn lipid peroxidation and increases resistance of red blood cells to oxidative hemolysis (Bekyarova, 1997).

In addition to promoting healing of wounds and burns, the PFC gel can also prevent scarring. Scars are created when there is not enough oxygen for the skin to correctly heal. Accordingly, increasing oxygen concentrations in the tissue can reduce the appearance of scars.

Therefore, the PFC gel can also prevent scarring by quickly healing minor wounds and reduce the appearance of scars by oxygenating the skin tissue and activating the skin regenerative function.

Similarly, the PFC gel can also be used for topical application after procedures causing tissue damage. For example, the PFC gel can be applied to post-surgery incisions to promote faster healing. Capillaries ultimately oxygenate the cells/tissues. After an injury (which includes surgical incisions), it's the capillaries that are damaged, making them incapable of carrying fluid to and from the damaged tissues. The result is swelling and inflammation.

Increased oxygen levels promote angiogenesis, the growth of new capillaries and the repair of damaged capillaries. Thus, oxygen would accelerate healing of the capillaries and fluid could then again be removed. The PFC gel would also oxygenate the tissues at the same time. When swelling is reduced, the pain caused by inflammation is also reduced. It is envisioned that any medical procedure which causes tissue injury could potentially benefit, e.g., pulling teeth, incisions, etc.

In another example, the PFC gel can be applied post-cosmetic surgery (e.g, post-microdermabrasion or chemical facial peels), both for the soothing effect as well as the acceleration of recovery. Since these procedures literally abrade/remove the top layers of the dermis, the PFC gel can then promotes cell turnover and repair, which should be accelerated by the topical use.

Similarly, the gel can be used to treat burns resulting from radiation in the same way that it treats burns in general as previously discussed.

The PFC gel can be a component of a combination therapy or an adjunct therapy. For example, the gel can be administered with or without hyperbaric or supplemental oxygen. In one embodiment, the subject can be administered the PFC gel disclosed herein in combination with supplemental oxygen. In another embodiment, the PFC gel can be administered in combination with the subject's own white blood cells, increasing the efficacy of the treatment.

Anti-Aging Cosmetic Use

The PFC gel can also be used as a cosmetic agent to promote anti-aging. The PFC gel can be used for reducing skin imperfections associated with aging such as fine lines and wrinkles. The PFC gel can also be used for scar reduction and promotion of skin firmness.

Oxygen levels in the skin decrease as we age, making the appearance of fine lines and wrinkles more noticeable. Applying an oxygen-rich gel can restore oxygen levels and prevent fine lines and wrinkles.

In addition, oxygen can inhibit the destructive enzyme collagenase which breaks down collagen. Collagen is one of the structural substances that supports the skin's surface. By supporting collagen production (by inhibiting collagenase through higher oxygen levels), the skin can be firmer and look more youthful.

Therefore, the PFC gel can diminish fine lines and wrinkles by using oxygen to activate the skin regenerative functions and collagen production. Moreover, the PFC gel can increase the firmness and elasticity of the skin by activating collagen and elastin creation.

Yet another cosmetic use for the PFC gel disclosed herein is the reduction of cellulite. By topically applying the PFC gel in combination with caffeine and optionally dimethyl sulfoxide (DMSO), cellulite can be reduced.

Treatment of Acne and Rosacea

The PFC gel can also be used to treat skin infirmities such as acne or rosacea. Specially, the PFC gel can prevent, heal and eliminate acne, providing clear & break-out free skin.

Acne is a dermatological condition that is thought to be caused by genetic factors, increased sebum production, abnormal keratinization of the hair follicle, host immune response, and due to the harmful effects of increased proliferation of the anaerobic bacteria *Propionibacterium acnes*. This type of bacteria is responsible for much of the inflammatory reaction that occurs in acne, thought to be due to its release of toxins. Inflammation occurs when *P. acnes*, growing in plugged follicles, releases chemoattractants eliciting the inflammatory response creating the classical comedones of acne. Therefore, the clinical manifestations appear to be the result of bacterial-induced inflammation of a plugged sebaceous gland. Inflammation is further enhanced by follicular rupture and subsequent leakage of lipids, bacteria, and fatty acids into the dermis. Systemic and topical antibiotics are used for both treatment and prophylaxis of acne. Treatments that reduce *P. acnes* numbers lead to clinical improvement of acne (Thiboutot, 1997) and, finally, to the emergence of antibiotic-resistant *P. acnes* strains are linked to the failure of antibiotic treatment (Eady et al, 1989).

Current treatment of acne consists of selection of a topical therapy which is based on the severity and type of acne. Topical retinoids, benzoyl peroxide, and azelaic acid are effective treatments for mild acne. Topical tretinoin (Retin-A) which is a derivative of vitamin A, and a comedolytic agent that normalizes desquamation of the epithelial lining, thereby preventing obstruction of the pilosebaceous outlet. This agent also appears to have direct anti-inflammatory effects. Topical antibiotics and medications with bacteriostatic and anti-inflammatory properties are effective for treating mild to moderate inflammatory acne. Systemic antibiotics are used for the moderate to severe patient. Isotretinoins is used to treat severe, often nodulocystic and inflammatory acne. Isotretinoin (Accutane) acts against the four pathogenic factors that contribute to acne. It is the only medication with the potential to suppress acne over the long term. To be able to prescribe this medication, the physician must be a registered member of the manufacturer's System to Manage Accutane-Related Teratogenicity (SMART) program. The SMART program was developed in conjunction with the U.S. Food and Drug Administration (FDA) to minimize unwanted pregnancies and educate patients about the possible severe adverse effects and teratogenicity of isotretinoin, which is a pregnancy category X drug.

Acne can be caused by an anaerobic bacterium infection as well as the inflammatory reaction caused by the release of the bacteria's toxins. Anaerobic bacteria are intolerant of oxygen, replicating at low oxidation-reduction potential sites. Since *Propionibacterium acnes* is an anaerobic bacterium, it thrives in an environment devoid of oxygen. The addition of oxygen to an anaerobic infection helps to kill the bacteria and improve the dermatological condition called acne. The PFC gel disclosed herein is able to carry a large amount of oxygen, up to approximately four times the amount of oxygen that hemoglobin can carry. The PFC gel is able to provide this oxygen through diffusion to an area of low oxygen concentration, such as an anaerobic infection.

Anaerobic bacteria are more susceptible to the effects of oxygen than the more common aerobic bacteria. The PFC gel when applied topically provides increased local oxygen to the acne lesions and helps eradicate *Propionibacterium acnes* and thus ameliorates the acne.

The introduction of supplemental topical oxygen (in an oxygenated perfluorocarbon or via diffusion through PFC) to a patient who has acne enables the intensity and number of lesions to be eradicated more efficiently than current therapeutic regiments. It helps decrease the extent, duration, super infections and complications (such as scarring) from acne.

Moreover, if large pores are a contributing factor to acne and blemishes, by providing an oxygen-rich environment to the pores, breakouts can be prevented by keeping the pores open and clean. The PFC gel therefore provides increased oxygen to the tissues, a healthy environment is created for cells, allowing them to multiply and thrive.

The application of the topical form of FtBu in a cream, gel, pomade, shampoo, conditioner, lotion, liquid, potion, foam, or similar product, or in combination with a topical antibiotic, or topical acne product such as retinoid, benzoyl peroxide, peroxide, isotretionoin, etc. to the inflamed and infected area enhances the eradication and prevention of the harmful effects of *Propionibacterium acnes*. In addition, the PFC Gel helps prevent, ameliorate and eradicate superinfections and some of the complications (comedones, pustules, papules, etc.) that acne causes.

Also the PFC gel can eliminate and/or reduce redness and pustules associated with rosacea breakouts. For this indication, the same principles described for acne and other uses apply. The PFC gel increases oxygen levels in the face and should be particularly effective because the capillary bed feeding the face is so vast and they are located very close to the surface of the skin. In addition, rejuvenation and healing mechanism described previously is also applicable.

Enhancement of Sexual Function

The PFC gel can also be used for enhancing sexual function. Specifically, the PFC gel can be topically used for increasing oxygen delivery to the sex organ of a subject for enhancement of male and female sexual function.

The PFC gel provides to the sex organ an oxygen-rich environment and thus improves sexual response time, the frequency of erections, and the duration of response. Specifically, the PFC gel can be applied topically to the sex organ and absorbed into local circulation, causing trabecular smooth muscles to relax, which is the mechanism leading to an erection.

Other Indications and Uses

Other indications and uses are summarized as follows:

Air Deodorizer:
The PFC gel can be used for elimination of unwanted odors, particularly in the kitchen or in the bathroom. Since PFCs are quick to absorb gases, it would instantly absorb methane gas that causes the bad odor which can then be quickly vented from the room. It is important to note that unlike many other deodorizers, the PFC gel eliminates odors and does not simply mask them.

Canker Sores:
The PFC gel can be used for reducing the time it takes to cure canker sores. Oxygen is known to help the immune system fight bacteria and infections. By increasing oxygen concentrations, the body's immune system would be able to fight infections better Cavities:
The PFC gel can be used in a cavity fighting mouthwash or toothpaste. At night, humans salivate less and therefore do not wash away food particles and harmful bacteria. These bacteria can make their ATP aerobically, but they switch to fermentation if there is no $O_2$ available. It is this fermentation that lowers the pH on the teeth and cases demineralization and decay. By increasing oxygen, the PFC gel can prevent the fermentation process from taking place.

Decubitus Ulcer:
The PFC gel can also be used in the treatment of decubitus ulcers, more commonly known as besores.
By packing the wound with gauze or other material containing the PFC gel or by coating the large surface area of these types of wounds with the PFC gel, the gel can accelerate healing of the wound from the inside out.

Diabetic Foot Care:
The PFC gel can be used in the treatment of the diabetic foot by providing an oxygen-rich environment to the diabetic foot as well as adding a protective barrier which may be provided by the surfactant, thus keeping the skin of the diabetic foot soft, preventing it from becoming dry and then cracking, which often leads to more serious foot wounds and infections.

Gas Gangrene:
The PFC gel can be used for fighting deadly infections caused by gas gangrene. Gas-producing organisms (such as those that cause toxic shock syndrome and gas gangrene and botulism) cause their damage by releasing toxic gases into the tissues/body. These organisms are anaerobic. Therefore, by providing an oxygen-rich environment, the anaerobic organisms would be destroyed by oxygen.
As an additional benefit, the PFC gel can absorb the toxic gases released from the organisms.

Hemorrhoids:
PFC gel disclosed herein can be used in the treatment of hemorrhoids, specifically, in relieving inflammation, reducing swelling and associated pain in addition to reducing incidence of necrosis. Hemorrhoids are varicose veins and as such, their blood supply is compromised. Application of an oxygen-enhancing gel will bring needed oxygen to the area, which will prevent necrosis of the tissues. Since inflammation is a response to tissue injury, and in this case, the injury is caused by limited oxygen supply, replenishing the oxygen supply would reduce the inflammation, thereby reducing the swelling and associated pain.

Muscle Pain/Aching Muscle:
The PFC gel can be used for the treatment of muscle pain. The gel can be applied to the muscles to provide oxygen before, during, or after strenuous exercise. In one embodiment, the gel can be combined with an ingredient which provides heat to the muscles, such as camphor or eucalyptus.
The gel can also be used for speeding up the healing process of muscle tears. Strenuous activity creates small tears in muscle tissue. The Healing of these tears increases muscle mass. The PFC gel will increase oxygen tension in the muscle and hence, speed up the healing process.

Nocturnal Leg Cramps:
PFC gel disclosed herein can be used in the treatment of nocturnal leg cramps by increasing oxygen levels in the lower leg during sleep.
Nocturnal leg cramps affect nearly 70% of the population. Various causes include dehydration, electrolyte imbalance and decreased oxygen to the limbs (also caused by various factors). Even when cramping is caused by dehydration/electrolyte imbalance, it is ultimately the decrease in oxygen, secondary possibly to the root cause that causes the muscles to cramp. Therefore, the PFC gel can be used in the treatment of nocturnal leg cramps by increasing oxygen levels in the lower leg during sleep.

Pruritus Relief:
The PFC gel can be used for pruritus relief and for providing faster healing of irritated skin.
The PFC gel can be used for pruritus relief resulting from insect bites, contact dermatitis eczema, etc. Studies have shown that oxygen may inhibit histamine release that is the cause of itch associated with various conditions. It has been disclosed that an oxygen-glucose deprived environment increases histamine release (Shen, 2007). Therefore, the gel can be used, e.g., for relieving pruritus. Specifically, for relieving itch from insect bites, poison ivy, etc.
The PFC gel can also treat inflammation associated with various conditions as previously described. Thus, the PFC gel would also reduce redness, swelling and irritation related to insect bites.
By increasing oxygen concentrations, pruritus and general skin irritation are alleviated. s an additional benefit, the PFC in the gel also anesthetizes skin similar to the way benzocaine does.

Reduction of Toxic Gases from Cigarettes:
The PFC gel can also be used in the reduction of toxic gases from cigarettes.
The toxic gases found in tobacco smoke include carbon monoxide, nitrogen oxides, hydrogen cyanide, ammonia, acrolein, freon, formaldehyde and many others. These toxins are partly responsible for conditions commonly seen in smokers, such as bronchitis and emphysema. Hydrogen cyanide was the gas used in gas chambers in WWII and is a known toxin to the central nervous system.
After absorption through the lungs, CO combines with hemoglobin in the red blood cells and reduces the amount of oxygen in the blood and tissues. CO combined with nicotine is believed to play a part in accelerating the deposition of cholesterol in the inner lining of arteries, which eventually leads to arteriosclerosis.
Impairment of blood flow and reduced oxygen carrying capacity due to CO reduce the supply of oxygen to the heart at the same time that the heart's need for oxygen is increased by the stimulant effect of nicotine on the rate and force of the heart's contractions, damaging the heart and increasing the severity of a heart attack.
CO+nicotine are also important factors in causing peripheral vascular disease, which can lead to gangrene of the feet.
By saturating the filter of cigarettes with Oxycyte™ emulsion or by injecting the PFC gel into the filter, the PFC binds many of the harmful/toxic gases found in tobacco smoke, trapping them in the filter and reducing the amount that is inhaled into the lungs. This provides the benefit of reducing harmful/irritating/toxic gases from smoking. In this application PFCs are contained in a filter so as to trap any burning PFCs can release dangerous chemicals.

Safety Equipment for Manufacturing Facilities:
  The PFC gel can also be used to absorb dangerous gases to prevent potential disasters arising from gas leaks in chemical manufacturing plants since PFCs are quick to absorb gases.
  In one embodiment, the PFC can be incorporated into sprinkler systems on site. In another embodiment, the PFC gel is sprayed in the gas-filled area in the same manner as a fire extinguisher. In this case, the toxic gases are quickly absorbed by the PFC gel and the gel is then hosed out of or otherwise removed from the room.

Shampoo, Conditioner, Dandruff or Hair Loss Treatment:
  The PFC gel can also be incorporated into hair products such as shampoo and conditioners, enhancing oxygen concentration when applied. Pollutants in the air are known to make hair drab and dull. By increasing oxygen to the hair, the hair would be revitalized.
  The gel would also moisturize hair and protects it from heat when styling. The gel can also reduce frizz in hair.
  At the same time, oxygenating and moisturizing the scalp creates a healthy and hydrated scalp. Having a healthy and hydrated scalp would reduce the likelihood of dandruff and therefore, of fungal colonization of the scalp that is often caused by dandruff.
  Moreover, the PFC gel can aid in hair growth. The PFC gel can increase generation of capillaries that feed the scalp, thereby increasing blood flow and oxygenation to hair follicles.

Skin Graft:
  The PFC gel can also accelerate skin graft uptake and increase in skin graft survival.
  For skin grafts, it is critical to restore the circulation to the grafted tissues as soon as possible. As discussed previously, oxygen promote angiogenesis, the growth of new capillaries and the repair of damaged capillaries. Again, it is the capillaries which feed the tissues by carrying fluid to and from the tissues.
  By topically applying the PFC gel and promoting angiogenesis, the gel can promote re-epithelialization, healing and graft acceptance by bringing additional oxygen to the epithelial cells.

The perfluorocarbon employed in the compositions and methods described herein may be in compositions which may further comprise pharmaceutically acceptable carrier or cosmetic carrier and adjuvant(s) suitable for topical administration. Compositions suitable for topical administration are well known in the pharmaceutical and cosmetic arts. These compositions can be adapted to comprise the oxygenated perfluorocarbon. The composition employed in the methods described herein may also comprise a pharmaceutically acceptable additive.

The multiplicity of configurations may contain additional beneficial biologically active agents which further promote tissue health.

The compositions of this invention may be administered in forms detailed herein. The use of perfluorocarbon may be a component of a combination therapy or an adjunct therapy. The combination therapy can be sequential or simultaneous. The compounds and compositions can be administered independently by the same route or by two or more different routes of administration depending on the dosage forms employed.

The dosage of the compounds and compositions administered in treatment will vary depending upon factors such as the pharmacodynamic characteristics of a specific therapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds and compositions may comprise a single compound or mixtures thereof with other compounds. The compounds can be introduced directly into the targeted tissue, using dosage forms well known to those of ordinary skill in the cosmetic and pharmaceutical arts.

The compounds and compositions can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical and cosmetic practices. The compounds can be administered alone but are generally mixed with a pharmaceutically acceptable carrier. This carrier can be a solid or liquid, and the type of carrier is generally chosen based on the type of administration being used. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The PFC compositions may contain the any of the following non-toxic auxiliary substances:

The PFC compositions may contain antibacterial agents which are non-injurious in use, for example, thimerosal, benzalkonium chloride, methyl and propyl paraben, benzyldodecinium bromide, benzyl alcohol, or phenylethanol.

The PFC compositions may also contain buffering ingredients such as sodium chloride, sodium acetate, gluconate buffers, phosphates, bicarbonate, citrate, borate, ACES, BES, BICINE, BIS-Tris, BIS-Tris Propane, HEPES, HEPPS, irnidazole, MES, MOPS, PIPES, TAPS, TES, and Tricine.

The PFC compositions may also contain a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, peanut oil, polyalkylene glycols, petroleum based jelly, ethyl cellulose, ethyl oleate, carboxymethyl-cellulose, polyvinylpyrrolidone, isopropyl myristate and other conventionally employed acceptable carriers.

The PFC compositions may also contain non-toxic emulsifying, preserving, wetting agents, bodying agents, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic.

The PFC compositions may also contain surfactants that might be employed include polysorbate surfactants, polyoxyethylene surfactants, phosphonates, saponins and polyethoxylated castor oils, but preferably the polyethoxylated castor oils. These surfactants are commercially available. The polyethoxylated castor oils are sold, for example, by BASF under the trademark Cremaphor.

The PFC compositions may also contain wetting agents commonly used in ophthalmic solutions such as carboxymethylcellulose, hydroxypropyl methylcellulose, glycerin, mannitol, polyvinyl alcohol or hydroxyethylcellulose and the diluting agent may be water, distilled water, sterile water, or artificial tears, wherein the wetting agent is present in an amount of about 0.001% to about 10%.

The formulation of this invention may be varied to include acids and bases to adjust the pH; tonicity imparting agents such as sorbitol, glycerin and dextrose; other viscosity imparting agents such as sodium carboxymethylcellulose, microcrystalline cellulose, polyvinylpyrrolidone, polyvinyl alcohol and other gums; suitable absorption enhancers, such as surfactants, bile acids; stabilizing agents such as antioxidants, like bisulfites and ascorbates; metal chelating agents, such as sodium edetate; and drug solubility enhancers, such as polyethylene glycols. These additional ingredients help make commercial solutions with adequate stability so that they need not be compounded on demand.

Finally, the formulation of this invention can be adjusted so that the PFC composition is the form of a cream, pomade, shampoo, conditioner, lotion, liquid, potion, foam, or similar product, which are suitable for topical application.

Other materials as well as processing techniques and the like are set forth in Part 8 of Remington's Pharmaceutical Sciences, 17th edition, 1985, Mack Publishing Company, Easton, Pa., and International Programme on Chemical Safety (IPCS), which is incorporated herein by reference.

All combinations of the various elements are within the scope of the invention.

It is understood that where a parameter range is provided, all integers within that range, and tenths thereof, are also provided by the invention. For example, "10-90 wt %" includes 10.0 wt %, 10.1 wt %, 10.2 wt %, 10.3 wt %, 10.4 wt % etc. up to 90.0 wt %.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Testing for Oxycyte™ Toxicity

An Oxycyte™ emulsion (60% wt/vol. PFC) was tested systemically via intravenous administration in Sprauge Dawley rats, Cynomolgus Monkeys and humans.

The Oxycyte™ emulsion was found to be well tolerated and had no toxicity.

Example 2

Stable Gels A-E

Summary

Five gel recipes, named Gels A-E, have been deemed most successful considering the stability and viscosity of the resulting gel. Each gel is composed of water, a surfactant (Pluronic F-68 or Pluronic F-127), and a perfluorocarbon (perfluorodecalin (PFD) or recycled perfluoro(tert-butylcyclohexane) (FtBu)). Experimental materials and procedures are described below as well as relevant percent yields.

Materials
1. Pluronic F-68: [Sigma-Aldrich P1300-500G Batch #097K0116 CAS 9003-11-6];
2. Pluronic F-127: [Sigma-Aldrich P2443-250G Batch #038K0113 CAS 9003-11-6];
3. Perfluorodecalin, 95% mixture of cis and trans (PFD): [Sigma-Aldrich T3251-100G Batch #078K1882 CAS 10191-41-0];
4. Recycled t-butylperfluorocyclohexane (FtBu): [Oxygen Biotherapeutics, Inc. Costa Mesa, Calif. 92626];
5. Ethyl Alcohol, absolute, 200 proof, 99.5%, A.C.S. reagent: [ACROS 61509-0040, CAS 64-17-5];
6. Distilled $H_2O$;
7. 20-100 mL glass beakers;
8. 5-20 mL glass beakers;
9. 20-50 mL Corning centrifuge tubes;
10. 5-60 mL Teflon capped, glass jars;
11. OMNI Macro ES Homogenizer;
12. 750 Watt, 20 kHz Ultrasonic Processor;
13. Fisherbrand Spoonulet Lab Spoon;
14. Spatula;
15. Pipet;
16. 5 mL NORM-JECT® luer lock, airtight syringe; and
17. B-D® 26 gauge ½ inch, luer lock, Precision Glide® syringe needle.

Experimental Procedures
GEL A 16.25 g of distilled water was weighed into a 100 mL glass beaker. 20 g of PFD was added to the beaker followed by 5 g of F-68. The contents of the beaker were then manually stirred with a spatula for 30 seconds. The tip of an OMNI Macro ES Homogenizer was submerged into the contents of the beaker, and the stirred mixture was homogenized for approximately 5 minutes at 4000 rpm. The homogenized mixture was poured into a 50 mL Corning centrifuge tube. The procedure was then repeated three times in order to prepare 4 centrifuge tubes. All 4 centrifuge tubes were centrifuged in an IEC Clinical Centrifuge for 30 minutes. The off-fluid of each tube was poured out and weighed separately. The gel remaining in each tube was scooped out using a Fisherbrand Spoonulet Lab Spoon and weighed into a 60 mL Teflon capped, glass jar. The jar was labeled GEL A.

GEL B 16.25 g of distilled water was weighed into a 100 mL glass beaker. 20 g of PFD was added to the beaker followed by 5 g of F-68. The contents of the beaker were then manually stirred with a spatula for 30 seconds. The tip of a 750 Watt, 20 kHz Ultrasonic Processor was submerged into the contents of the beaker, and the stirred mixture was sonicated for approximately 5 minutes at 20% amplitude. The sonicated mixture was poured into a 50 mL Corning centrifuge tube. The procedure was then repeated three times in order to prepare 4 centrifuge tubes. All 4 centrifuge tubes were centrifuged in an IEC Clinical Centrifuge for 30 minutes. The off-fluid of each tube was poured out and weighed separately. The gel remaining in each tube was scooped out using a Fisherbrand Spoonulet Lab Spoon and weighed into a 60 mL Teflon capped, glass jar. The jar was labeled GEL B.

GEL C 16.25 g of distilled water was weighed into a 100 mL glass beaker. 20 g of FtBu was added to the beaker followed by 5 g of F-127. The contents of the beaker were then manually stirred with a spatula for 30 seconds. The tip of an OMNI Macro ES Homogenizer was submerged into the contents of the beaker, and the stirred mixture was homogenized for approximately 5 minutes at 4000 rpm. The homogenized mixture was poured into a 50 mL Corning centrifuge tube. The procedure was then repeated three times in order to prepare 4 centrifuge tubes. All 4 centrifuge tubes were centrifuged in an IEC Clinical Centrifuge for 30 minutes. The off-fluid of each tube was poured out and weighed separately. The gel remaining in each tube was scooped out using a Fisherbrand Spoonulet Lab Spoon and weighed into a 60 mL Teflon capped, glass jar. The jar was labeled GEL C.

GEL D 16.25 g of distilled water was weighed into a 100 mL glass beaker. 20 g of FtBu was added to the beaker followed by 5 g of F-127. The contents of the beaker were then manually stirred with a spatula for 30 seconds. The tip of a 750 Watt, 20 kHz Ultrasonic Processor was submerged into the contents of the beaker, and the stirred mixture was sonicated for approximately 5 minutes at 20% amplitude. The sonicated mixture was poured into a 50 mL Corning centrifuge tube. The procedure was then repeated three times in order to prepare 4 centrifuge tubes. All 4 centrifuge tubes were centrifuged in an IEC Clinical Centrifuge for 30 minutes. The off-fluid of each tube was poured out and weighed separately. The gel remaining in each tube was scooped out using a Fisherbrand Spoonulet Lab Spoon and weighed into a 60 mL Teflon capped, glass jar. The jar was labeled GEL D.

GEL E 16.25 g of distilled water was weighed into a 100 mL glass beaker. 20 g of FtBu was added to the beaker followed by 5 g of F-68. The contents of the beaker were then manually stirred with a spatula for 30 seconds. The tip of an OMNI Macro ES Homogenizer was submerged into the contents of the beaker, and the stirred mixture was homogenized for approximately 5 minutes at 4000 rpm. The homogenized mixture was poured into a 50 mL Corning centrifuge tube. The procedure was then repeated three times in order to prepare 4 centrifuge tubes. All 4 centrifuge tubes were centrifuged in an IEC Clinical Centrifuge for 30 minutes. The off-fluid of each tube was poured out and weighed separately. The gel remaining in each tube was scooped out using a Fisherbrand Spoonulet Lab Spoon and weighed into a 60 mL Teflon capped, glass jar. The jar was labeled GEL E.

Determination of Perfluorocarbon Yields

Approximately 5 g of each gel was placed individually into 20 mL glass beakers. Using a pipet, 2.80 g, 2.90 g, 7.00 g, 6.32 g, and 5.48 g of ethanol were added to each beaker containing Gel A, Gel B, Gel C, Gel D, and Gel E, respectively. Each gel/ethanol mixture was stirred for 5 minutes using a spatula. Each stirred mixture was allowed to sit for 3 minutes in order for two layers, an aqueous layer and a perfluorocarbon layer, to separate. The perfluorocarbon layer was removed from the beaker using a 5 mL syringe with a 26 gauge, 2 inch syringe needle. The weight of the perfluorocarbon layer was recorded. This weight divided by the initial (~5 g) gel weight for each gel sample gave the perfluorocarbon yield for each gel.

Results

Yield Data

The perfluorocarbon yield is defined as the percentage of perfluorocarbon added during the preparation that remained as part of the recovered gel. The perfluorocarbon yields were as follows.

|  | Percent |
|---|---|
| Gel A | 95.8 |
| Gel B | 94.0 |
| Gel C | 48.8 |
| Gel D | 34.1 |
| Gel E | 90.8 |

The percent gel yield is defined as the total weight of recovered gel relative to the total weight of components added during preparation. The gel yields were as follows.

|  | Percent |
|---|---|
| Gel A | 65.8 |
| Gel B | 85.6 |
| Gel C | 43.8 |
| Gel D | 40.0 |
| Gel E | 40.5 |

Example 3

Stable Gels 1-4

Table 1 shows four preferred embodiments of the subject invention (Gels 1-4).

TABLE 1

| | grams/gram of gel | | | |
|---|---|---|---|---|
| Component | Gel 1<br>75, 25 - T | Gel 2<br>75, 25 - H | Gel 3<br>$(PQ)^2$ - T | Gel 4<br>$(PQ)^2$ - H |
| perfluoro(tert-butylcyclohexane) | 85.980% | 86.726% | 85.980% | 86.726% |
| Distilled Water | 10.277% | 10.366% | 10.277% | 10.366% |
| Pluronic ® F-68 | 0.307% | 0.310% | 0.307% | 0.310% |
| Pluronic ® L-35 | 2.446% | 2.467% | 2.446% | 2.467% |
| Polyquaternium-6 | 0.000% | 0.000% | 0.248% | 0.033% |
| Polyquaternium-7 | 0.743% | 0.099% | 0.495% | 0.066% |
| EDTA | 0.248% | 0.033% | 0.248% | 0.033% |

Pluronic® is a trade name of BASF Corporation (Mt. Olive, N.J.). Pluronic F-68 and Pluronic L-35 are hydroxyl-terminated ethylene oxide-propylene oxide block copolymers. They have the general formula: $HO(C_2H_4O)_a(C_3H_6O)_b(C_2H_4O)_cH$. Subscripts a and c are usually about equal and subscript b is usually 15 or higher. F-68 is a solid with a molecular weight of about 8400; L-35 is a liquid with a molecular weight of about 1900.

The chemical structures for Polyquaternium-6 and Polyquaternium-7 are shown below:

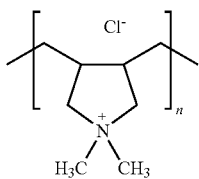

Polyquaternium 6 ionic surfactant/preservative
Poly(diallyldimethylammonium chloride)
(CAS No. 26062-79-3) (Nalco Merquat® 100)

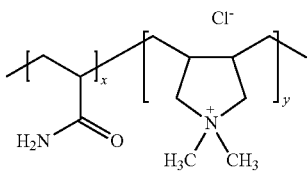

Polyquaternium 7 ionic surfactant/preservative
Poly(acrylamide-co-diallyldimethylammonium chloride)
(CAS No. 26590-05-06) (Nalco Merquat® 740)

These materials are sold by several companies including Nalco Company of Naperville, Ill. Both chemicals contain highly polar dimethylammonium chloride quaternary salts. There are many other polyquat salts as shown in Table 2. However, not all are used as preservatives.

TABLE 2

| Product | CAS RN |
|---|---|
| polyquaternium 1 | 75345-27-6 |
| polyquaternium 2 | 68555-36-2 |
| polyquaternium 4 | 92183-41-0 |
| polyquaternium 5 | 26006-22-4 |
| polyquaternium 6 | 26062-79-3 |
| polyquaternium 7 | 26590-05-6 |
| polyquaternium 10 | 68610-92-4 |
| polyquaternium 11 | 53633-54-8 |
| polyquaternium 12 | 68877-50-9 |
| polyquaternium 13 | 68877-47-4 |
| polyquaternium 14 | 27103-90-8 |
| polyquaternium 15 | 35429-19-7 |
| polyquaternium 16 | 95144-24-4 |
| polyquaternium 22 | 53694-17-0 |
| polyquaternium 24 | 107987-23-5 |
| polyquaternium 28 | 131954-48-8 |
| polyquaternium 31 | 136505-02-7 |
| polyquaternium 32 | 35429-19-7 |
| polyquaternium 33 | 69418-26-4 |
| polyquaternium 37 | 26161-33-1 |
| polyquaternium 44 | 150599-70-5 |
| polyquaternium 46 | 174761-16-1 |
| polyquaternium 57 | 9004-97-1 |

EDTA is ethylene diamine tetraacetic acid. The disodium salt and tetrasodium salt of EDTA are more frequently used than the tetraacid as cosmetic preservatives. However, these salts (in fact, any ionizable salt) will break the gel or prevent the gel from forming.

The concentrations of the three preservatives are based either on the total basic gel weight (including the FtBu), designated "-T" gels or the concentration is based on the weight of the water and Pluronics only, designated "-H" gels. The 75, 25-T gel (Gel 1) contains 7500 ppm of Polyquat-7 and 2500 ppm of EDTA, both based on the total formulation weight including the FtBu. Gel $(PQ)^2$-H (Gel 4) contains 2500 ppm PQ-6, 5000 ppm PQ-7, and 2500 ppm EDTA—each based on the weight of the aqueous phase in the gel only.

Gel Formation and Processing

The formation of gels 1-4 proceeds by first mixing the aqueous phase components (distilled water, F-68, L-35, and the preservatives of choice) in a glass, polyethylene, PET, or 316 stainless steel vessel. The mixture is homogenized for about 5 minutes with a rotor/stator homogenizer at 10,000-35,000 RPM. The homogenizer can be handheld for small samples (<2 L), a bench top unit for larger (2-5 L) samples, or a larger, floor mounted version of these mixers for commercial scale production (>5 L).

During mixing of the aqueous phase, not all components need be completely soluble. The F-68 has limited solubility in water and homogenization mostly disperses this solid as very fine particles once the saturation limit for F-68 in water has been reached. Similarly, high concentrations of EDTA can result in a fine particle dispersion after the solubility limit for EDTA in water has been attained (-500 ppm in water at 20° C.).

After homogenization of the aqueous phase mixture, the perfluorocarbon (PFC) is added either in aliquots or slowly and continuously over the course of the next 10-30 minutes of high speed homogenization. Gel formation tends to occur only at the latter stages of PFC addition. The gels that form do not require centrifugation and separation as taught by Moore in U.S. Pat. No. 4,569,784, which is hereby incorporated by reference herein.

Continued homogenization past the 25-30 minutes typical for gel formation creates more viscous gels. For some formulations, the long term stability of the gel improves with longer mixing. The formulations which will exhibit this behavior can be determined by trial and error. Other PFC gels can be obtained by this process. For example, very stable gels can be formed using APF-200 (available from Exfluor Corporation, Round Rock, Tex.) or perfluorodecalin in similar recipes. This method is anticipated to be applicable to a wide range of perfluorocarbon solvents and, possibly, to hydrofluorocarbons or hydrochlorofluorocarbons.

Factors Affecting Gel Formation and Processing

There are many compounds and materials that are incompatible with the disclosed gels.

Alcohols

Trace levels of alcohols will immediately or eventually cause the gel to break. The inventors have observed this behavior with trace amounts of methanol, ethanol, isopropanol, tecopherol, chlorhexidine digluconate, chlorphenesin, and glycerol. It appears that any compound having a primary, secondary, or tertiary hydroxyl or phenolic group will break the gel or prevent the formation of the gel.

Highly Ionized salts

Highly ionized compounds (salts) can prevent the formation of the gel or break the gel once formed. While low levels (<5000 ppm) of EDTA can be incorporated successfully, the di- and tetrasodium salts of EDTA prevent formation. Tap water contains sufficient levels of ions to break the gel in a period of 1-24 hours after contact. While polymeric quaternary ammonium compounds have been successfully added, benzalkonium chloride will prevent gel formation at ppt levels or lower. If highly ionized salts contact the gel after formation, the salts can break the gel even if not mechanically mixed into the bulk. It is often sufficient for gel destruction to contact one surface of the gel with a quiescent aqueous puddle of the offensive compound. Once the gel begins to break, it tends to continue to unravel over a period of hours to days.

Highly Nonpolar Solid Surfaces

Highly nonpolar solid surfaces are incompatible with these gels and will break the gels quickly or over time. This occurs whenever the perfluorocarbon can "wet" a solid surface and form a film of the pure PFC. The film tends to segregate gravitationally and sink slowly to the bottom of the vessel holding the gel. This process "renews" or frees the surface to contact more gel and separate more PFC. The process continues slowly until a large part of the gel has broken and formed two distinct phases. The inventors have observed this behavior for packaging films having heat seal lacquer coatings and for Teflon® surfaces. Teflon is an especially aggressive gel breaker. Thus far, it appears that glass, polyethylene, PET, nylon, and other non-PFC wettable surfaces are compatible with the gels.

Metal Surfaces

Certain metal surfaces are incompatible with gels but for differing reasons. Aluminum surfaces are easily wetted by the PFC and cause separation and eventually breaking of the gels. 304 stainless steel, unlike 316 stainless, is attacked and corroded by the gels. The surface of 304 stainless is passivated by an oxide coating that is easily breached by the chloride anion of the polyquat salts. Once breached, the surface is attacked by the EDTA and corroded. It is anticipated that other incompatible metals will be observed with more testing. Clearly, the choice of materials of construction is important for commercial production of these gels.

Packaging Materials

Some packaging materials are inappropriate for the gels. In particular, those plastics that are highly permeable to water will be poor choices since loss of the aqueous phase by diffusion through the plastics will degrade and eventually break the gels. A good example is PET. A single layer of PET will allow water in the gel to escape. However, if PET is sandwiched with polyethylene or polypropylene, the poor solubility of water in the polyolefins will lower the permeation loss rate to an acceptable level and the gel will remain secure.

Example 4

Measuring Oxygen Tension in Tissue

A material which binds oxygen (fluorescent marker) is injected into skin tissue. The combination is fluorescent and the more oxygen that is present, the stronger the fluorescent signal. (representing the oxygen tension in the tissue).

First it is determined that fluorescence chemistry is unaffected by the PFCs and poloxamers. Then as a control, the fluorescent marker is injected into the skin, and oxygen tension is obtained. Finally, the same area is treated with a PFC or a PFC gel and oxygen tension is again obtained.

Result: oxygen tension reading begins to spike after injection of the marker into the area treated with PFC, then starts to decline as the PFC is eliminated from the tissue.

Conclusion: the absorption of an oxygen-binding PFC like FtBu or APF-200 substantially increases local oxygen tension in the tissue. The resulting increase in local oxygen concentration may serve both to increase rates of wound healing and rates of free-radical deactivation.

Example 5

Wound and Burn Healing and Scar Prevention and Reduction

Example 5A

A perfluorocarbon gel composition as described herein is administered topically to a subject. Specifically, the gel is administered topically to a wound on the subject.

The PFC gel increases oxygen level and oxygen tension in the wound tissue. In addition, the gel accelerates wound healing. Moreover, the perfluorocarbon is well tolerated and has no toxicity.

Example 5B

A perfluorocarbon gel composition as described herein is administered topically to a subject. Specifically, the gel is administered topically to a burn wound on the subject.

The PFC gel increases oxygen level and oxygen tension in the burnt tissue and surrounding tissue. In addition, the gel accelerates the healing of the burn wound. Moreover, the perfluorocarbon is well tolerated and has no toxicity.

Example 5C

A perfluorocarbon gel composition as described herein is administered topically to a subject. Specifically, the gel is administered topically to a wound or a scar on the subject.

The PFC gel increases oxygen level and oxygen tension in the wound or scarred tissue. In addition, the gel accelerates wound healing and ameliorates and reduces the appearance of the scar. Moreover, the perfluorocarbon is well tolerated and has no toxicity.

Example 6

Promotion of Anti-Aging

Example 6A

A perfluorocarbon gel composition as described herein is administered topically to a subject. Specifically, the gel is administered topically to the skin on the subject.

The PFC gel increases oxygen level and oxygen tension in the skin tissue. In addition, the gel reduces the appearance of skin imperfection associated with aging including fine lines and wrinkles. Also, the gel improves the firmness of the skin where applied. Moreover, the perfluorocarbon is well tolerated and has no toxicity.

Example 6B

A perfluorocarbon gel composition as described herein mixed with caffeine is administered topically to a subject. Specifically, the gel mixture is administered topically to the cellulite-affected skin on the subject.

The PFC gel mixture increases oxygen level and oxygen tension in the skin tissue. In addition, the gel mixture reduces the appearance the cellulite where applied. Moreover, the perfluorocarbon is well tolerated and has no toxicity.

Example 7

Treatment of Acne and Rosacea

Example 7A

A perfluorocarbon gel composition as described herein is topically administered to the skin of a subject suffering from acne at the site of the acne. Topical administration of the PFC gel is effective to treat the subject's acne. Acne reduction is noticeable, as is a reduction in skin appearance characteristics associated with acne.

Example 7B

A perfluorocarbon gel composition as described herein is topically administered to the skin a subject suffering from acne vulgaris at the site of the acne vulgaris. Topical administration of the PFC gel is effective to reduce acne-scarring in the subject by reducing the severity of existing acne vulgaris and preventing or reducing the severity of further acne vulgaris in the subject.

Example 7C

A perfluorocarbon gel composition as described herein is topically administered a subject suffering from a *Propionibacterium acnes* infection of a skin follicle of the subject. The composition is applied to the skin follicle or the area of skin surrounding the skin follicle. Topical administration of the PFC gel is effective to reduce the *Propionibacterium acnes* infection of the skin follicle of the subject.

Example 7D

A perfluorocarbon gel composition as described herein is topically administered to the skin of a subject suffering from a *Propionibacterium acnes* infection of the dermis of the subject. The composition is applied to the skin comprising the infected dermis. Topical administration of the PFC gel is effective to reduce the *Propionibacterium acnes* proliferation in the dermis of the subject.

Example 7E

A perfluorocarbon gel composition as described herein is topically administered to the skin of a subject susceptible to acne. Topical administration of the PFC gel is effective to prevent or reduce the subject's acne.

Example 7F

A perfluorocarbon gel composition as described herein is topically administered to the skin of a subject wherein there are *Propionibacterium acnes* in and/or on the skin. Topical administration of the PFC gel is effective to kill *Propionibacterium acnes* in and/or on the skin of the subject.

In the above examples the administration of the composition is one, two or three times per day. The administration can be repeated daily for a period of one, two, three or four weeks, or longer. The administration can be continued for a period of months or years as necessary.

Example 7G

A perfluorocarbon gel composition as described herein is topically administered to the skin of a subject suffering from rosacea at the site of the rosacea. Topical administration of the composition comprising the perfluorocarbon or oxygenated perfluorocarbon is effective to treat the subject's rosacea. Rosacea reduction is noticeable, as is a reduction in skin appearance characteristics associated with rosacea.

Example 8

Sexual Enhancement

Example 8A

A perfluorocarbon gel composition as described herein is administered topically to sex organs of a human male subject. Local oxygen tension and nocturnal erections are evaluated. Changes in Quality of life (QOL) data is also collected and assessed.

Oxygen level and oxygen tension in the tissue increases. In addition, Quality of life of the subject improves. Moreover, the perfluorocarbon is well tolerated and has no toxicity.

Example 8B

A perfluorocarbon gel composition as described herein is topically administered to sex organs of male and female human subjects. The PFC gel is administered once or twice daily. Local oxygen tension and nocturnal erections (in males) are evaluated. Changes in Quality, of life (QOL) data is also collected and assessed.

Oxygen level and oxygen tension in the tissue is increases. In addition, Quality of life of the subject improves. Moreover, the perfluorocarbon composition is well tolerated and has no toxicity.

References
1. U.S. Pat. No. 4,569,784, issued Feb. 11, 1986 to Robert E. Moore.
2. Bekyarova, G., et al. (1997) "Suppressive effects of FC-43 perfluorocarbon emulsion on enhanced oxidative haemolysis in the early postburn phase." *Burns.* (23)2: 117-121.
3. Davis, Stephen C., et al. (2007) "Topical Oxygen Emulsion: A Novel Wound Therapy" *Arch Dermatol.* 143(10): 1252-1256.
4. Eady et al., (1989) "Erythromycin resistant propionibacteria in antibiotic treated acne patients: Association with therapeutic failure" Br J Dermatol. 1989 July; 121(1):51-7.
5. Kaneda, Megan M., et al. (2009) "Perfluorocarbon nanoemulsions for quantitative molecular imaging and targeted therapeutics" *Ann Biomed Eng.* 37(10) October 2009. NDN 230-1024-9131-6.
6. Shen, Yao, et al. (2007) "Carnosine attenuates mast cell degranulation and histamine release induced by oxygen-glucose deprivation" *Cell Biochemistry and Function.* 26(3):334-338.
7. Thiboutot et al., (1997) "Acne. An overview of clinical research findings" *Dermatol Clin.* 1997 January; 15(1):97-109.

What is claimed is:

1. A perfluorocarbon gel composition comprising 84-90 wt % perfluorocarbon and 8-11 wt % water and 2-4 wt % surfactants relative to the total weight of the gel, wherein the perfluorocarbon is perfluoro(tert-butylcyclohexane).

2. The perfluorocarbon gel composition of claim 1, wherein the surfactants include polyoxyethylene-polyoxypropylene block copolymers.

3. The perfluorocarbon gel composition of claim 2, wherein the polyoxyethylene-polyoxypropylene block copolymers include Poloxamer 105 and/or Poloxamer 188.

4. The perfluorocarbon gel composition of claim 1, wherein the composition further comprises 0.01-6 wt % Vitamin E.

5. The perfluorocarbon gel composition of claim 4, wherein the composition comprises 0.03 wt % Vitamin E.

6. The perfluorocarbon gel composition of claim 1, wherein the composition further comprises 0.02-3.20 wt % preservatives.

7. The perfluorocarbon gel composition of claim 1, wherein the composition comprises 90 wt % perfluorocarbon, 8 wt % water, and 2 wt % surfactants.

8. The perfluorocarbon gel composition of claim 1, wherein the composition comprises 86.86 wt % perfluorocarbon, 10.42 wt % water, 2.69 wt % surfactants and 0.03 wt % Vitamin E.

9. The perfluorocarbon gel composition of claim 8, wherein the composition comprises 86.86 wt % perfluoro (tert-butylcyclohexane), 10.42 wt % water, 2.43 wt % Poloxamer 105, 0.26 Wt % Poloxamer 188 and 0.03 wt % Vitamin E.

10. The perfluorocarbon gel composition of claim 1, characterized by that it continuously delivers oxygen to a tissue at a rate of 0.2 cc/hour –20.0 cc/hour for up to 24 hours.

11. The perfluorocarbon gel composition of claim 10, wherein the composition continuously delivers oxygen to the tissue at a rate of 2.0 cc/hour for 24 hours.

12. The perfluorocarbon gel composition of claim 1, further comprising urea hydrogen peroxide.

13. A process of manufacturing the perfluorocarbon gel composition of claim 1 comprising the steps:

a) mixing water and surfactants—as an aqueous phase in a vessel;
b) homogenizing the mixture;
c) adding perfluorocarbon to the mixture over time during high speed homogenization; and
d) obtaining the gel.

14. The process of claim 13, wherein in step a) the aqueous phase include distilled water, as said water, surfactants, and further optionally, preservatives.

15. The process of claim 13, wherein in step a) the vessel is a glass, polyethylene, PET, or stainless steel vessel.

16. The process of claim 13, wherein in step b) the homogenizer is a rotor stator homogenizer.

17. The process of claim 13, wherein in step b) the mixture is homogenized for 4-6 minutes.

18. The process of claim 17, wherein step b) the mixture is homogenized for 5 minutes.

19. The process of claim 13, wherein in step b) the mixture is homogenized at 10,000-35,000 RPM.

20. The process of claim 13, wherein in step c) the perfluorocarbon is added in aliquots or continuously over 10-30 minutes.

21. The perfluorocarbon gel composition of claim 1, comprising 84-90 wt % perfluorocarbon, 9-11 wt % water, and 2-4 wt % surfactants, and 0.02-3.20 wt % preservatives relative to the total weight of the gel.

22. The perfluorocarbon gel composition of claim 21, wherein the surfactants are polyoxyethylene-polyoxypropylene block copolymers.

23. The perfluorocarbon gel composition of claim 22, wherein the polyoxyethylene-polyoxypropylene block copolymers include Poloxamer 105.

* * * * *